United States Patent
Lampropoulos et al.

(10) Patent No.: US 7,520,869 B2
(45) Date of Patent: Apr. 21, 2009

(54) SELF-SUTURING ANCHOR DEVICE FOR A CATHETER

(75) Inventors: Fred P. Lampropoulos, Sandy, UT (US); Arlin Dale Nelson, Sandy, UT (US); Darryl Kent Bachman, Salt Lake City, UT (US); Gregory R. McArthur, Sandy, UT (US); Thomas D. Stout, Salt Lake City, UT (US); Brian Stevens, Pleasant Grove, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 674 days.

(21) Appl. No.: 11/082,170

(22) Filed: Mar. 16, 2005

(65) Prior Publication Data
US 2006/0095008 A1    May 4, 2006

Related U.S. Application Data

(60) Provisional application No. 60/623,502, filed on Oct. 29, 2004, provisional application No. 60/627,485, filed on Nov. 12, 2004.

(51) Int. Cl.
*A61M 5/32* (2006.01)

(52) U.S. Cl. .................................................. 604/180

(58) Field of Classification Search ......... 604/174–180, 604/116–117; 606/139–153; 43/85–87
See application file for complete search history.

(56) References Cited

U.S. PATENT DOCUMENTS

| | | | |
|---|---|---|---|
| 2,669,231 A | 2/1954 | Fisher | |
| 4,221,215 A * | 9/1980 | Mandelbaum | ............... 604/327 |
| 4,372,073 A | 2/1983 | Goldman | |
| 4,717,385 A * | 1/1988 | Cameron et al. | ............ 604/174 |
| 4,869,719 A | 9/1989 | Hogan | ........................ 604/174 |
| 4,874,380 A | 10/1989 | Hesketh | ...................... 604/180 |
| 5,224,935 A | 7/1993 | Hollands | ..................... 604/180 |
| 5,416,952 A | 5/1995 | Dodge | |
| 5,911,229 A | 6/1999 | Chodorow | |
| 6,138,866 A | 10/2000 | Lambelet, Jr. et al. | |

(Continued)

OTHER PUBLICATIONS

US Office Action for U.S. Appl. No. 11/535,454 dated Jul. 28, 2008.

(Continued)

*Primary Examiner*—Nicholas D. Lucchesi
*Assistant Examiner*—Rebecca E Eisenberg
(74) *Attorney, Agent, or Firm*—Ryan D. Benson; Stoel Rives, LLP

(57) ABSTRACT

A self-suturing anchor device includes a base having a securement mechanism. The securement mechanism includes one or more resilient pockets in which are placed a plurality of looped sutures. The securement mechanism and looped sutures facilitate automatic securement of a catheter relative to the self-suturing anchor device. In at least one embodiment, the looped sutures are also threaded through loops in another corresponding looped suture, such that each looped sutures slidably tighten in concert with one another. When at least a portion of the securement mechanism is moved, at least one of the plurality of looped sutures is tensioned and closes against a securement point on the catheter. A catheter can be secured in a self-suturing anchor device in a quick and efficient manner with minimal effort.

20 Claims, 13 Drawing Sheets

U.S. PATENT DOCUMENTS

| | | | |
|---|---|---|---|
| 6,554,297 | B2 | 4/2003 | Phillips et al. |
| 2001/0037119 | A1 | 11/2001 | Schmieding |
| 2002/0002324 | A1 | 1/2002 | McManus |
| 2002/0072713 | A1* | 6/2002 | Almond et al. ........ 604/167.05 |
| 2003/0229313 | A1* | 12/2003 | Bierman .................... 604/174 |
| 2006/0095009 | A1 | 5/2006 | Lampropoulos et al. |

OTHER PUBLICATIONS

US Office Action for U.S. Appl. No. 11/202,484 dated Jul. 29, 2008.
US Office Action for U.S. Appl. No. 11/532,056 dated Jul. 29, 2008.

* cited by examiner

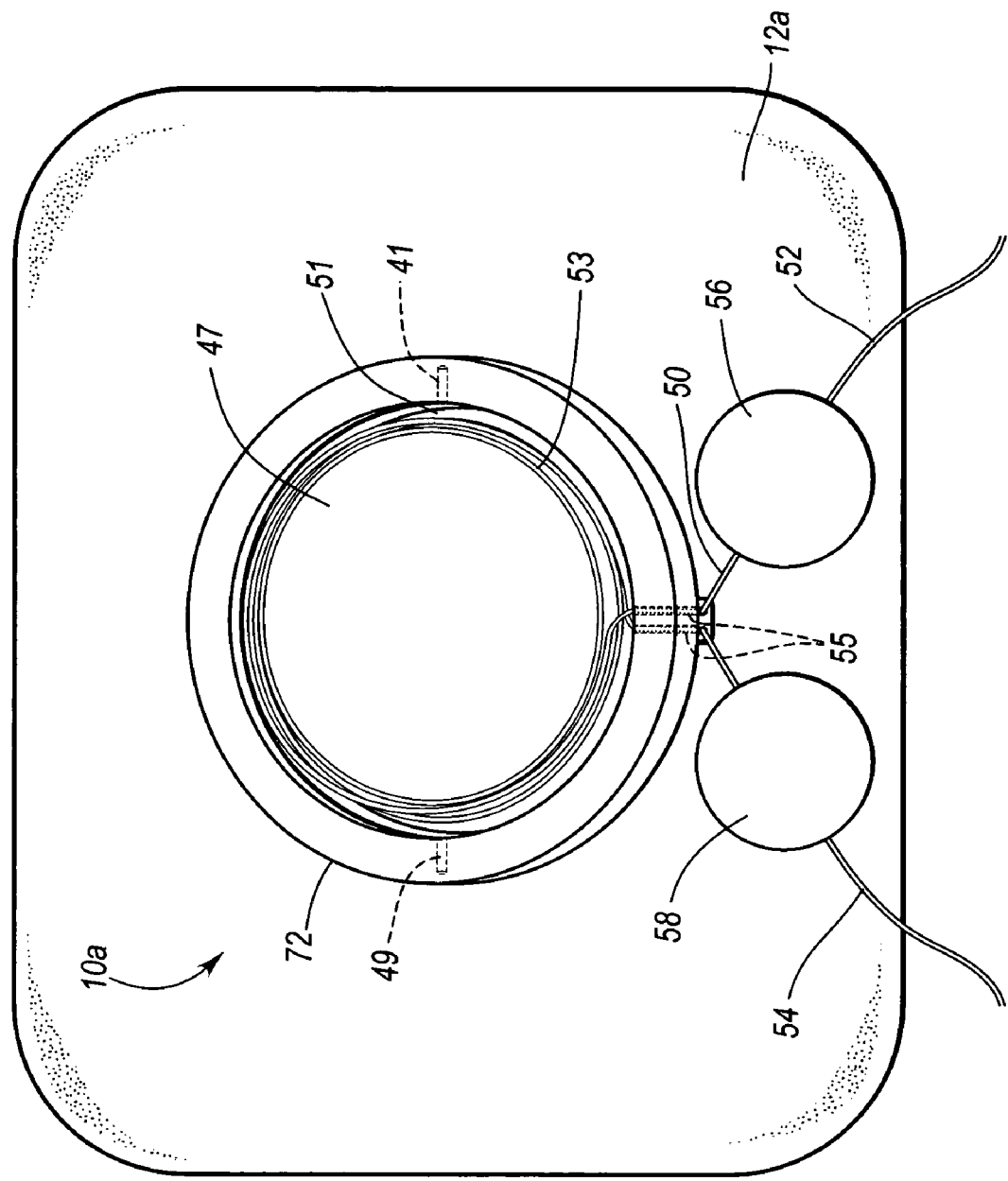

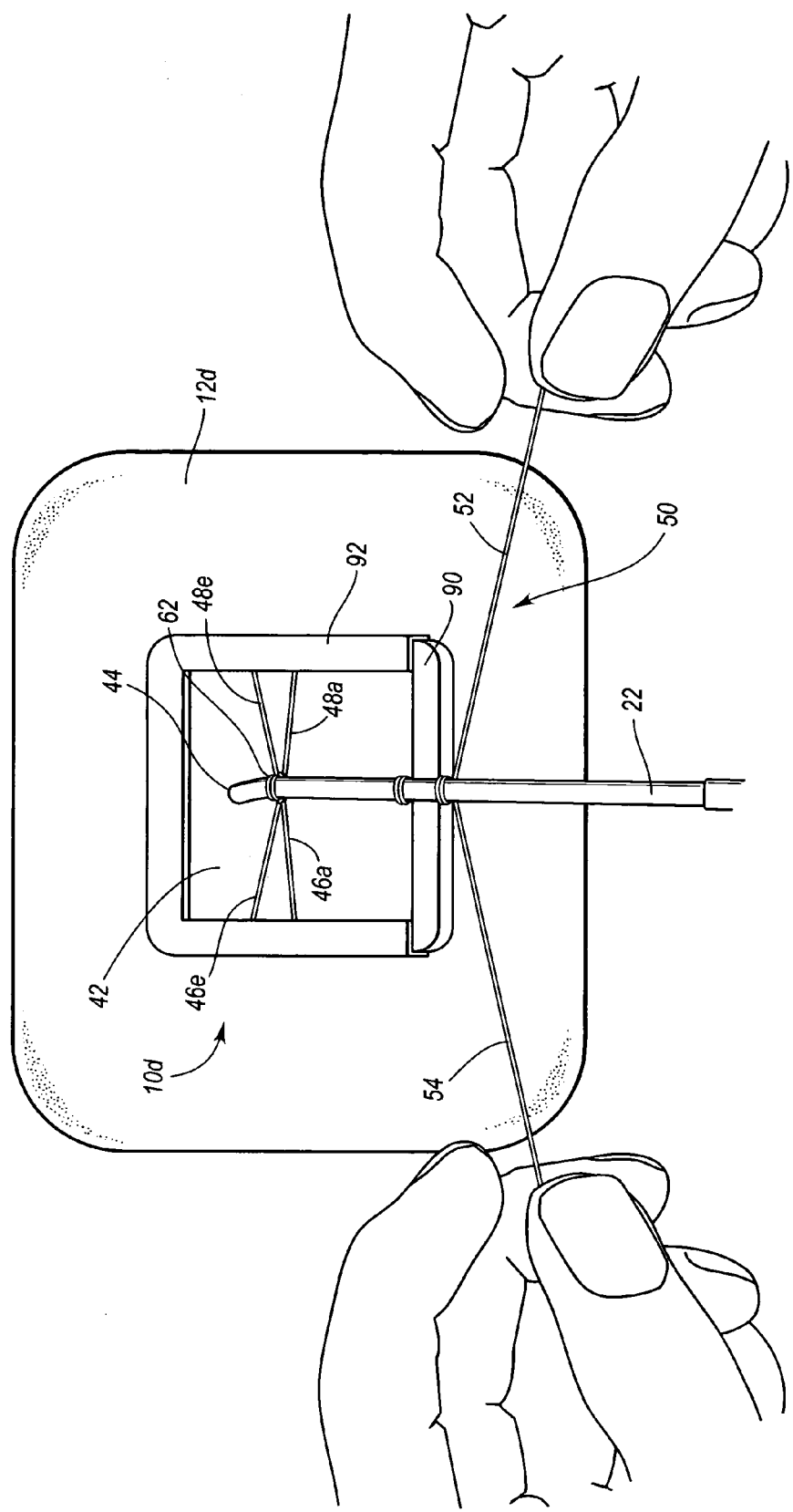

SELF-SUTURING ANCHOR DEVICE FOR A CATHETER

CROSS-REFERENCE TO RELATED APPLICATIONS

This application claims the benefit of priority to U.S. Provisional Patent Application No. 60/623,502, filed on Oct. 29, 2004, entitled "Self-suturing Anchor Device for a Catheter"; and to U.S. Provisional Patent Application No. 60/627,485, filed on Nov. 12, 2004, entitled "Self-suturing Anchor Device for a Catheter", the entire specifications of both applications are incorporated herein by reference.

BACKGROUND OF THE INVENTION

1. The Field of the Invention

Exemplary embodiments of the present invention relate to the field of catheters, and, more particularly, to a self-suturing anchor device for use with a catheter.

2. Background and Relevant Art

Catheters play an important role in the treatment and care of patients in modern medicine. In particular, catheters provide relatively unobtrusive access to remote portions of a patient's body, allowing desired procedures or treatments to be performed.

A wide variety of generalized and specialized catheters have been developed and refined for particular uses. For example, angioplasty catheters have been adapted to provide a safe and effective conduit for the delivery of a stent and/or balloon to a narrowing or blockage in a patient's artery or vein. Drainage catheters are configured to be inserted into a cavity surrounding a patient's kidney, liver or other organ to drain excess fluid or infection from the cavity.

In addition, a number of devices and implements have been developed for use with catheters, to facilitate their effectiveness, or to overcome inherent difficulties associated with their use. For example, catheters that are designed to remain placed in a patient for long periods of time, such as for ongoing care or treatment of the patient, present a number of difficulties. Such catheters must be secured to the patient in a manner that minimizes movement of the catheter that could harm the patient, or otherwise interrupt proper functioning of the catheter.

Accordingly, one approach in the prior art has been to suture the catheter directly to the patient's skin. However, when a patient repositions himself/herself in bed, the catheter may pull at the suture site or bend the catheter. Another approach is to inflate a balloon associated with the distal end of the catheter inside the patient. However, at times an incoherent patient may attempt to withdraw or otherwise remove the catheter. This can cause injury to the catheter insertion site, or can interfere with proper operation of the catheter.

In view of these and other problems in the art, a number of devices have been developed to secure a catheter in a manner that minimizes movement of the catheter, or minimizes interference with its proper operation. Typically, such devices include an adhesive layer to be secured to the patient with a small bore for accommodating the catheter and an adhesive strip to secure the catheter relative to the adhesive layer. Devices such as these are useful because they can be employed by a practitioner to secure the desired positioning of the catheter. Such devices, however, can be undesirable due at least in part to the fact that they typically obstruct the catheter insertion site. This can make it difficult to identify infections, drainage, or other complications that may occur at the catheter insertion site. Furthermore, the devices can also obstruct cleaning of the insertion site, such that the site can only be cleaned by removing the anchor devices. Additionally, conventional anchor devices typically utilize a clip, or other securement member which typically is rigid or has a high profile when utilized to secure the catheter. As a result, the securement device can be uncomfortable if pressed against the patient by a chair, bed, or other object.

FIG. 1 illustrates a modified version of an anchor device 10 that has been conventionally utilized by practitioners to secure a catheter. Anchor device 10 comprises a stoma covering that is modified by a practitioner to secure a catheter. Such stoma coverings are typically used to secure a drainage bag, such as a colostomy, illeostomy, or other similar such ostomy bag. Anchor device 10 includes an adhesive sheet 12, a semi-rigid ring 14, a sealing layer 16, and a center aperture 18. Adhesive sheet 12 provides a mechanism for securing anchor device 10 to a patient.

Adhesive sheet 12 also secures semi-rigid ring 14 in a desired position relative to the stoma, catheter, or article or apparatus to be secured to the patient. Semi-rigid ring 14 facilitates securing of a catheter, drainage bag, or other article or apparatus. Sealing layer 16 is positioned beneath and radially inward from semi-rigid ring 14, and covers a substantial portion of the bottom surface of anchor device 10. The inner boundary of sealing layer 16 defines center aperture 18. Sealing layer 16 provides a fluid tight seal with the patient to minimize leakage of bodily fluids outside of center aperture 18. Sealing layer 16 is somewhat resilient, or otherwise deformable, to thereby conform anchor device 10 to the patient's body around the stoma. Sealing layer 16 can include adhesive properties to maintain sealing contact with the patient.

The illustrated stoma covering also includes an adhesive backing (not shown) provided on the back side of sealing layer 16, and another adhesive backing (not shown) provided on the back side of adhesive sheet 12. The practitioner removes the adhesive backing from sealing layer 16 and adhesive sheet 12, and thereafter positions anchor device 10 on the patient's skin so that catheter 22 is within center aperture 18.

A practitioner modifies the conventional stoma covering by first removing the portion of sealing layer 16 that is positioned radially inward from semi-rigid ring 14. The portion of sealing layer 16 positioned radially inward from semi-rigid ring 14 can be removed utilizing a scalpel, scissors, or other implement. The practitioner then threads a first suture 24 from a right side 34 of semi-rigid ring 14 to a securement point 28 on catheter 22, and wraps first suture 24 around catheter 22 utilizing a first double-wrapped suture configuration 38. The practitioner then threads first suture 24 from catheter 22 to a left side 32 of semi-rigid ring 14, and then once again back to catheter 22. The practitioner then uses another double-wrapped suture configuration 40 to secure first suture 24 to catheter 22, such that the two double-wrapped suture configurations 38 and 40 define securement point 28. The second end of suture 24 is then threaded to right side 34 of semi-rigid ring 14, and tied to the first end of suture 24.

Once the practitioner has affixed suture 24 to securement point 28, the practitioner then secures catheter 22 to the bottom of semi-rigid ring 14 by first securing second suture 26 to catheter 22 adjacent bottom 36 of semi-rigid ring 14 on one side of semi-rigid ring 14. The practitioner then threads second suture 26 through the wall of semi-rigid ring 14 to an opposing side of semi-rigid ring 14. Second suture 26 is then secured to catheter 22 on the opposing side of semi-rigid ring 14. Done in this manner, catheter 22 is directly secured on both opposing surfaces of bottom 36 of semi-rigid ring 14 such that movement of the portion of catheter 22 associated with second securement point 30 is minimized.

One will appreciate, therefore, that sutures 24 and 26 can provide more stability and control of catheter 22 than would otherwise be provided by a single suture. For example, first suture 24 anchors catheter 22 to both left side 32 and to right side 34 of semi-rigid ring 14 to provide lateral stability to catheter 22 relative to a catheter insertion site. Furthermore, second suture 26 minimizes movement of the portion of catheter 22 associated with second securement point 30, such that catheter 22 does not pivot relative to securement point 28 in a manner that could result in lateral forces, pressure and/or tearing at the catheter insertion site. In addition, this arrangement allows access to the catheter insertion site and the inner boundary of semi-rigid ring 14 without obstruction. Such access allows a practitioner to identify and/or care for potential problems without needing to remove or reposition the anchor device 10.

While anchor device 10 provides advantages over other catheter securement devices, anchor device 10 presents a number of disadvantages in operation. For example, anchor device 10 is modified after the catheter is inserted into the patient. The time required to modify the anchor device and subsequently secure the catheter can add a significant amount of time to the catheter insertion procedure (e.g., 10-15 minutes or more). This can be uncomfortable for the patient in routine procedures. In more complex surgical procedures this can interfere with other aspects of the procedure to be performed, thus increasing the time the patient is under anesthesia. Additionally, the cost of the surgery is increased due to increased operating room and personnel time.

BRIEF SUMMARY OF THE INVENTION

The present invention relates to a self-suturing anchor device for a catheter. The self-suturing anchor device automatically secures the catheter without requiring the practitioner to manually suture the catheter to the self-suturing anchor device. The self-suturing anchor device has a securement mechanism which is adapted to be actuated by the user to automatically secure the catheter in a quick and efficient manner.

In one embodiment, a rotatable ring is provided in connection with the self-suturing anchor device to automatically secure the catheter. A pair of suture threads extends from the bottom of the rotatable ring. When a user pulls the threads in a rearward direction, the threads automatically secure a portion of the catheter associated with the bottom of the rotatable ring. The user can then rotate the rotatable ring in one of a clock-wise or a counter clock-wise direction. Rotation of the rotatable ring automatically secures the portion of the catheter positioned centrally within the rotatable ring. In one embodiment, a locking mechanism is utilized to maintain a secured position of the rotatable ring, and thus securement of the catheter.

The configuration of the rotatable ring and the suture threads provide automatic, quick, and efficient securement of the catheter. Securement in this manner shortens the length of the procedure and simplifies securement of the catheter such that an assisting nurse can perform securement of the catheter while the physician attends to other aspects of the procedure to be performed. Additionally, in some long term care circumstances the design and operability of the anchor device is sufficiently simple that the patient, family member, or home health care provider may be authorized to change the device at home or with minimal medical supervision. In another embodiment, the securement device comprises a square shaped member having a sliding member associated therewith. In this embodiment, movement of the sliding member automatically secures the catheter in a manner as similar to rotation of the rotatable ring.

In one embodiment of the invention, opposing suture loops are embedded within a resilient pocket of the rotatable ring. The suture loops are formed with a knot or other similar member for securing one end of the suture to a middle length of the suture to form the loop. The knot or member is adapted to allow sliding of the suture thread relative to the knot (slip knot) or other loop forming member. Additionally, a portion of the loop is threaded through the knot, or member of the knot, of the other loop. Shortening of both loops by rotating the rotatable ring draws the opposing knots/member toward opposing sides of the catheter.

The end of each suture opposite the loops is secured to a binding point on the wall of the rotatable ring. The sutures are threaded through the wall of the fixed base of the ring. Thus, when the rotatable ring is rotated, the binding point pulls the suture end of each individual suture loop along the circumference of base of the rotatable ring. Pulling of the suture ends decreases the size of the loops resulting in loops that are smaller than the circumference of the rotatable ring. As a result, the suture loops are deployed from their embedded position in the flexible resilient pocket of the rotatable ring. As the anchor device is rotated further, the loops of each suture tighten about the catheter, thereby securing the catheter in place. Additional sutures can also be utilized with the anchor device providing additional securement of the catheter relative to the self-suturing anchor device.

Additional embodiments described herein relate to variations on the anchor device, and different methods for drawing the suture loops about the catheter. According to the present invention, deployment of the securement devices can be effectuated quickly and effectively with minimal training and/or effort. Furthermore, the present invention allows a practitioner or other care provider to easily view the treatment site on the patient, thereby allowing the practitioner to treat or clean the site as needed without having to release or remove the catheter from the anchor device.

Additional features and advantages of exemplary embodiments of the invention will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 3B is a perspective view of the self-suturing anchor device of FIG. 2, illustrating the orientation of a first suture positioned within a resilient pocket;

DETAILED DESCRIPTION OF THE PREFERRED EMBODIMENTS

The present invention extends to a self-suturing anchor device for a catheter. The self-suturing anchor device automatically secures the catheter without requiring the practitioner to manually suture the catheter to the self-suturing anchor device. The self-suturing anchor device has a securement mechanism which is adapted to be actuated by the user to automatically secure the catheter in a quick and efficient manner.

Figure 1:
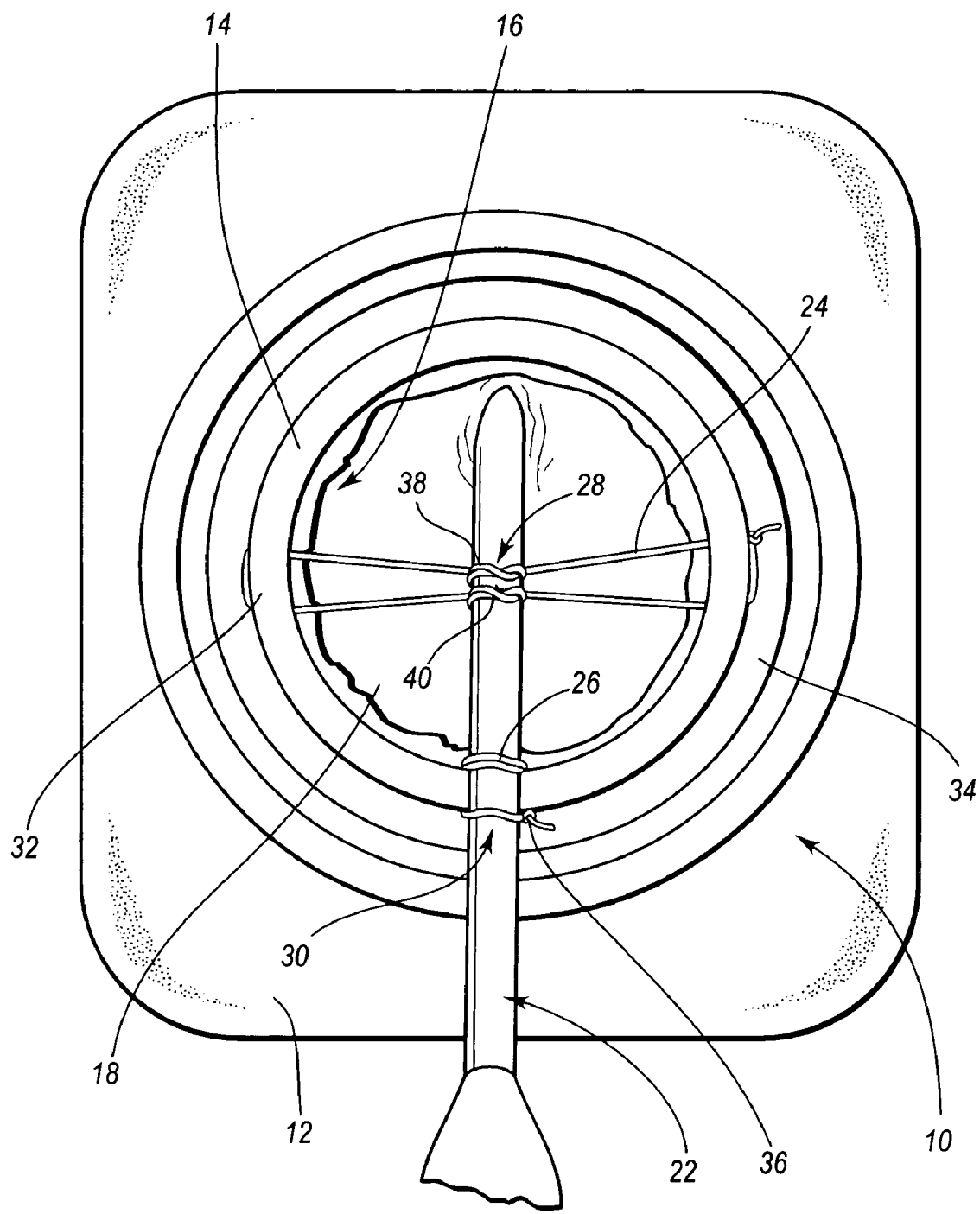
FIG. 1 illustrates a top view of a prior art anchor device modified for securing a catheter to a patient.
Figure 2:
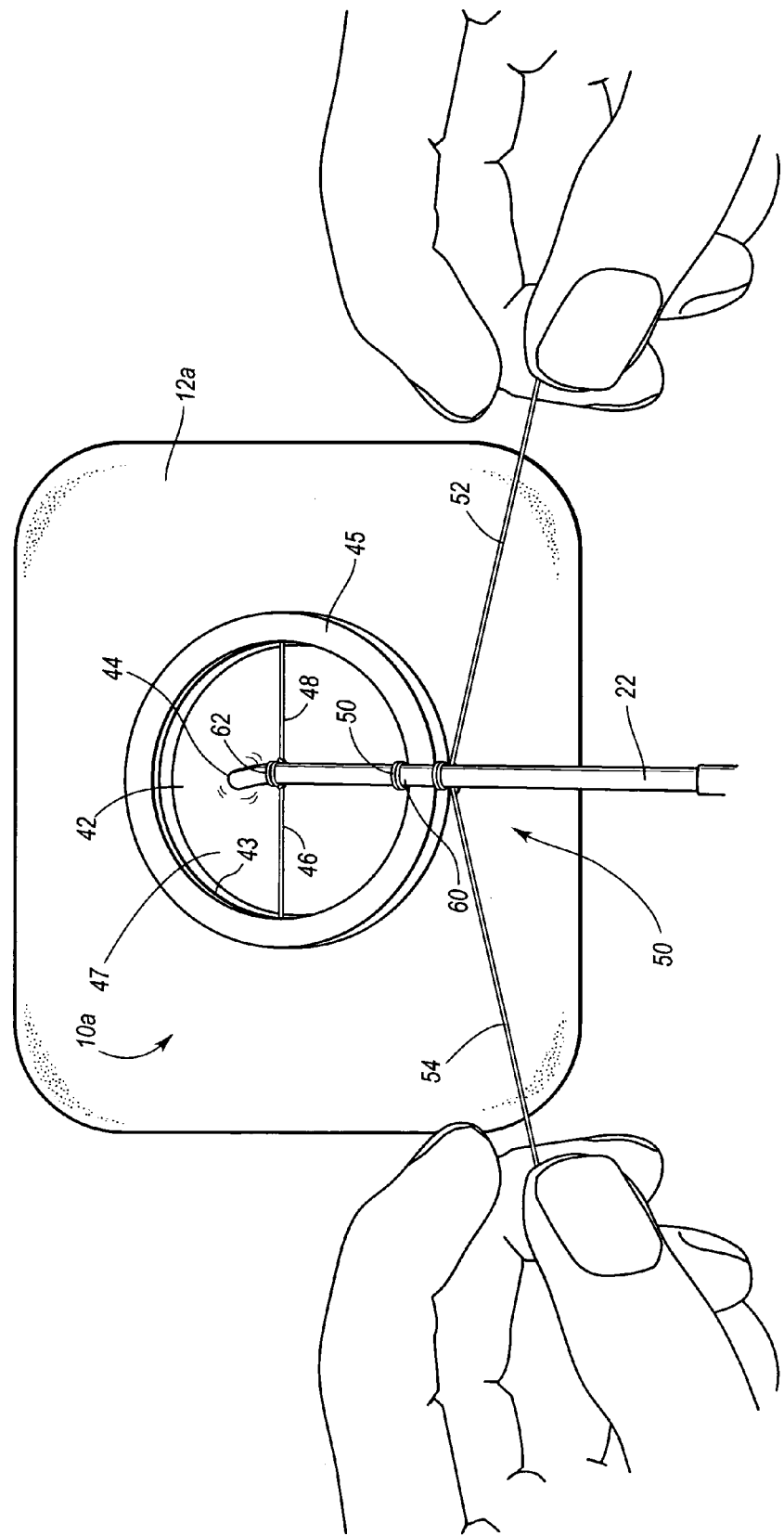
FIG. 2 illustrates a self-suturing anchor device in accordance with the present invention in a secured configuration after deployment of a securement mechanism.

FIG. 2 illustrates a self-suturing anchor device 10a having a rotatable ring 45 adapted to automatically secure a catheter 22 to self-securing anchor device 10a with a plurality of sutures 46, 48 and 50 in a quick and efficient manner. In the illustrated embodiment, catheter 22 has been inserted into and secured relative to a patient site 42. Movement of catheter 22 can cause discomfort, or even injury, to a catheter insertion site 44 of patient site 42. This can be particularly problematic when catheter insertion site 44 is at a location where catheter 22 will frequently be in contact with the patient's clothing, or in contact with a support surface, such as a chair or bed, on which the patient is resting. Self-suturing anchor device 10a of the present invention is adapted to automatically secure catheter 22 to self-suturing anchor device 10a to minimize movement of catheter 22.

In the illustrated embodiment, anchor device 10a includes an adhesive sheet 12a having a central aperture 47, a rotatable ring 45, a resilient pocket 43, a first suture 50, a second suture 46, and a third suture 48. Adhesive sheet 12a is adapted to secure anchor device 10a to a patient. Rotatable ring 45 is rotatably linked to adhesive sheet 12a and associated with resilient pocket 43, as described below. Resilient pocket 43 is adapted to receive and house sutures 46, 48 and 50 therein, and allow selective deployment of sutures 46, 48 and 50 therefrom. First, second and third sutures 50, 46 and 48 are embedded within resilient pocket 43 and are adapted to secure catheter 22 to self-suturing anchor device 10a. When suture 50 is pulled and rotatable ring 45 is subsequently rotated, sutures 50, 46 and 48 are deployed from resilient pocket 43 and automatically secure catheter 22 to anchor device 10a in a quick and efficient manner.

To secure catheter 22, a user first pulls a first end 52 and a second end 54 of first suture 50 to secure catheter 22 to rotatable ring 45 at a bottom securement point 60. The user then rotates rotatable ring 45 to deploy second suture 46 and third suture 48. Deployment of sutures 46 and 48 secure catheter 22 to self-suturing anchor device 10a at a center securement point 62. The present invention allows a user to quickly and efficiently secure a catheter relative to a patient. Additionally, the intuitive nature of the self-suturing anchor device 10a permits the self-suturing anchor device 10a to be operated by an assisting nurse or other skilled assistant allowing the physician to attend to other aspects of the procedure.

As will be appreciated by those skilled in the art, a variety of types and configurations of self-suturing anchor devices can be utilized without departing from the scope and spirit of the present invention. For example, in one embodiment the self-suturing anchor device is actuated by a mechanism other than a rotatable ring. In another embodiment, the resilient pocket does not entirely circumscribe the circumference of the rotatable ring. In another embodiment, the anchor device utilizes mechanisms other than sutures to secure the catheter. In another embodiment, anchor device utilizes a plurality of resilient pockets.

Figure 3:
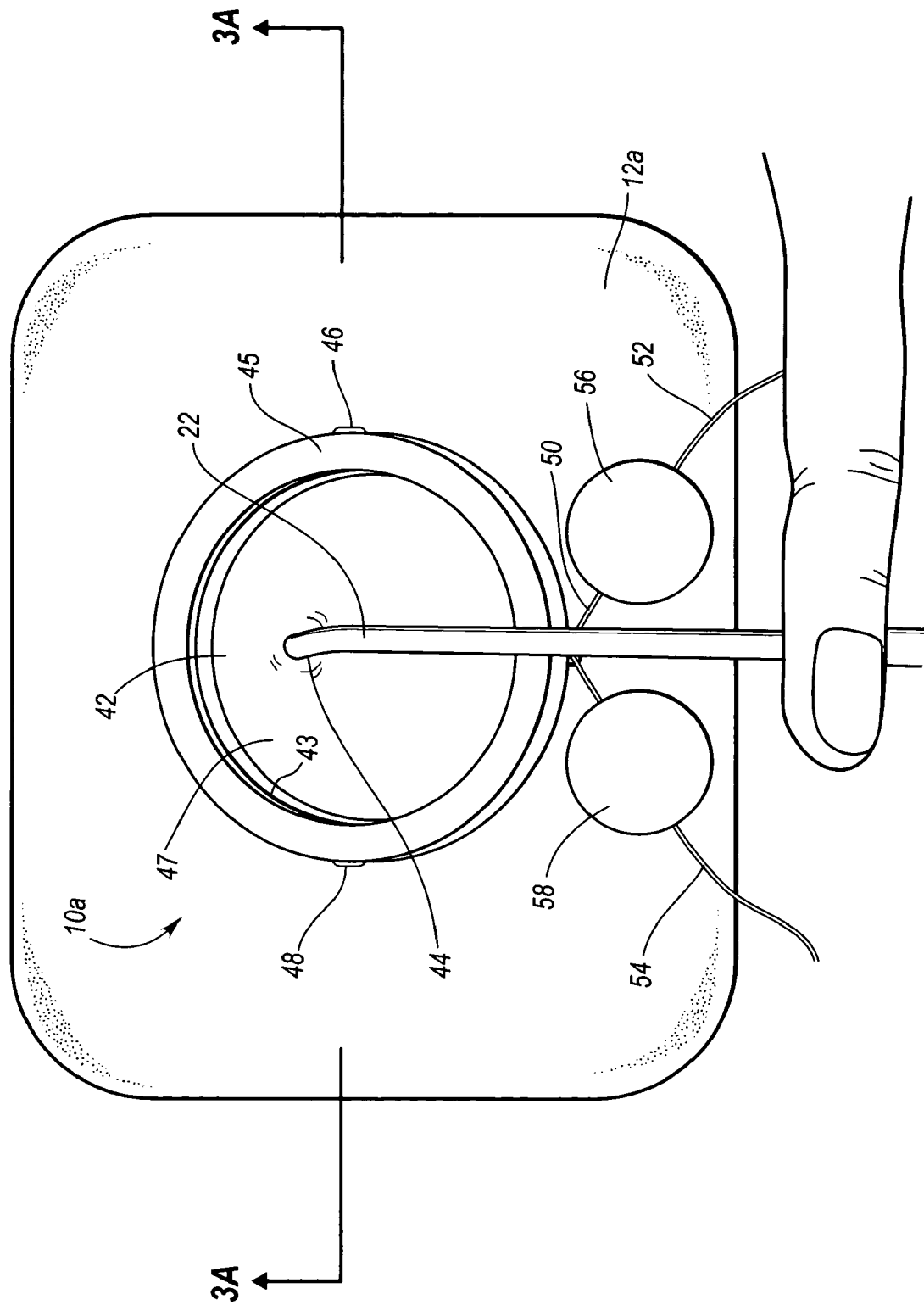
FIG. 3 illustrates the self-suturing anchor device of FIG. 2 prior to deployment of the securement mechanism.

FIG. 3 illustrates self-suturing anchor device 10a prior to deployment of sutures 46, 48 and 50. Central aperture 47 is adapted to allow catheter 22 to pass through anchor device 10a without obstruction. Anchor device 10a is secured to a patient with catheter insertion site 44 positioned approximately in the center of central aperture 47. Adhesive sheet 12a secures anchor device 10a to the patient to minimize movement of anchor device 10a once it is in the desired position. In the illustrated embodiment, first end 52 and second end 54 of first suture 50 are secured to adhesive sheet 12a by adhesive tabs 56 and 58. In preparation for securing catheter 22 with self-suturing anchor device 10a, a practitioner manipulates catheter 22 such that an intermediate portion of catheter 22 contacts rotatable ring 45. Such positioning of catheter 22 relative to rotatable ring 45 is advantageous for securement of catheter by sutures 46, 48 and 50 subsequent to deployment.

Figure 3A:
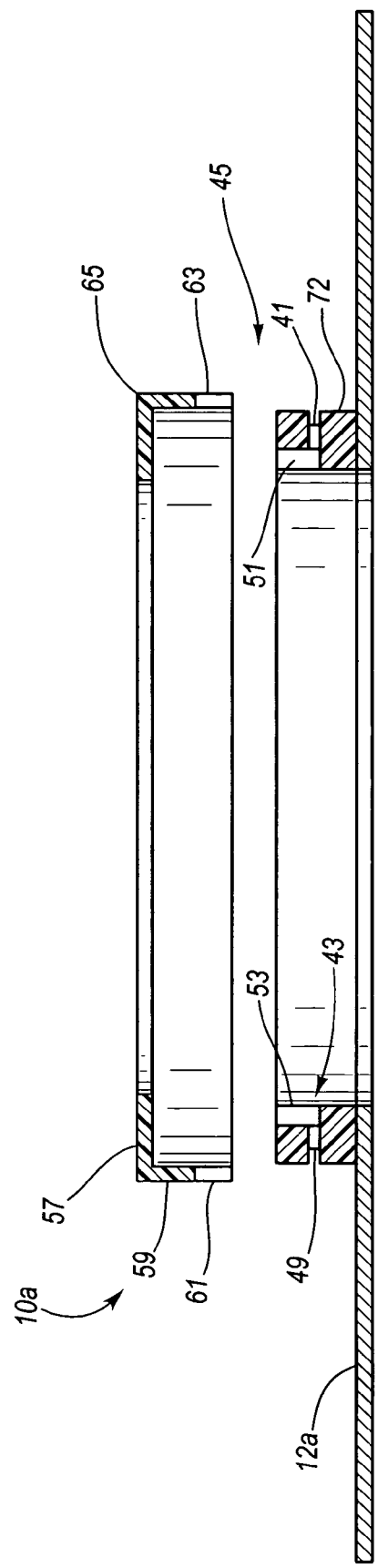
FIG. 3A is an exploded cross-section view of the self-suturing anchor device of FIG. 2.

FIG. 3A depicts an exploded cross-section view of self-suturing anchor device 10a detailing one embodiment of rotatable ring 45. In the illustrated embodiment, rotatable ring 45 comprises a rotatable outer ring 65 and a stationary inner ring, or base 72. Rotatable outer ring 65 is configured to be utilized with base 72, such that rotatable outer ring 65 can be rotated relative to base 72. Base 72 is secured to adhesive sheet 12a and includes resilient pocket 43, a first suture channel 51 (not shown), a second suture channel 41 and a third suture channel 49. Resilient pocket 43 includes a recess 51 and a resilient flange 53. Recess 51 and resilient flange 53 are configured to receive, house and retain sutures 46, 48 and 50 therein, and to allow selective deployment of sutures 46, 48 and 50 therefrom when sufficient force is exerted on sutures 46, 48 and 50. Recess 51 extends circumferentially along the periphery of base 72. Resilient flange 53 is positioned radially along the inner circumference of base 72. When rotatable outer ring 65 is positioned on base 72, resilient flange 53 is configured to retain sutures 46, 48 and 50 within recess 51 until sufficient force is exerted on sutures 46, 48 and 50. A sufficient force exerted on sutures 46, 48 and 50 causes resilient flange 53 to deflect. Deflection of resilient flange 53 allows deployment of sutures 46, 48 and 50 from recess 51.

Rotatable outer ring 65 includes a cap portion 57 and a ring portion 59. In the illustrated embodiment, ring portion 59 includes an inner surface and an outer surface concentric with the inner surface. The inner surface of rotatable outer ring 65 is configured to interface with an outer surface of base 72, such that rotatable outer ring 65 is positionable on base 72 and can rotate relative to base 72. Cap portion 57 is configured to interface with a top surface of base 72 to substantially enclose recess 51 when rotatable outer ring 65 is positioned on base 72. Rotatable ring 45 further includes a first slot 61 and an opposing second slot 63 formed in the ring portion 59 of rotatable outer ring 65. First and second slot 61 and 63 are configured to receive a suture therethrough to secure second and third suture 46 and 48 to rotatable ring 45.

FIG. 3B illustrates the orientation of first suture 50 within recess 51. In the illustrated embodiment, first suture 50 is positioned within recess 51 and first suture channel 55. First suture channel 55 extends from recess 51 through base 72 to the outside surface of base 72. First suture channel 55 is configured to receive a suture therethrough. In the illustrated embodiment, first suture channel 55 includes two channels. First end 52 of first suture 50 is secured to adhesive sheet 12a by adhesive tab 56 and is received in first suture channel 55. First suture 50 is looped twice around central aperture 47 and is received back into first suture channel 55. Second end 54 of first suture 50 extends from first suture channel 55 and is secured to adhesive sheet 12a by adhesive tab 58. The orientation of first suture 50 within recess 51 facilitates deployment of first suture 50 to automatically secure a catheter.

Figure 3C:
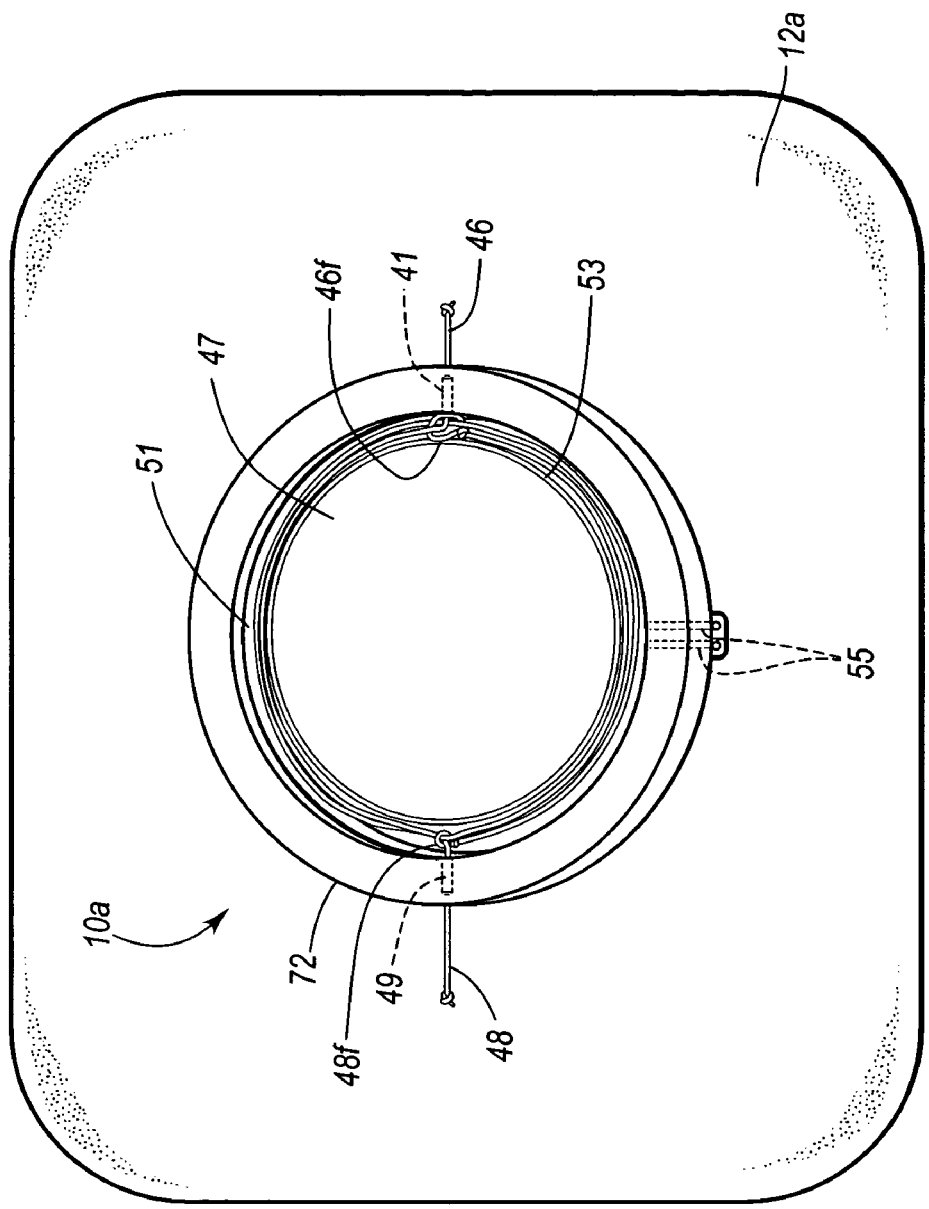
FIG. 3C is a perspective view of the self-suturing anchor device of FIG. 2, illustrating the orientation of a second and third suture positioned within the resilient pocket.

FIG. 3C illustrates the orientation of second and third suture 46 and 48 within recess 51. In the illustrated embodiment, second suture channel 41 extends from recess 51 through base 72 to the outside surface of base 72. Likewise, opposing third suture channel 49 extends from recess 51 through base 72 to the outside surface of base 72. Second and third suture channel 41 and 49 are configured to receive a suture therethrough. Second suture 46 is received in second suture channel 41, loops once around central aperture 47, and then terminates forming a slip knot 46f. A portion of second suture 46 is received within slip knot 46f to form a loop in second suture 46. Third suture 48 is received in third suture channel 49 and threaded through slip knot 46f as third suture 48 loops once around central aperture 47. Third suture 48 terminates forming a slip knot 48f. A portion of third suture 48 is threaded through slip knot 48f to form a loop in third suture 48. Additionally, a portion of second suture 46 is received within slip knot 48f. Thus, slip knots 46f and 48f each receive a portion of second suture 46 and third suture 48 therethrough. Terminal ends of second and third suture 46 and 48 are illustrated extending from suture channels 41 and 49, respectively. Terminal end of second suture 46 is configured to be received and retained within second slot 63 of rotatable ring 45 to secure second suture 46 to rotatable ring 45. Terminal end of third suture 48 is configured to be received and retained within first slot 61 of rotatable ring 45 to secure third suture 48 to rotatable ring 45. The orientation and configuration of second suture 46 and third suture 48 allow automatic securement of a catheter when rotatable ring 45 is rotated relative to base 72.

Figure 4:
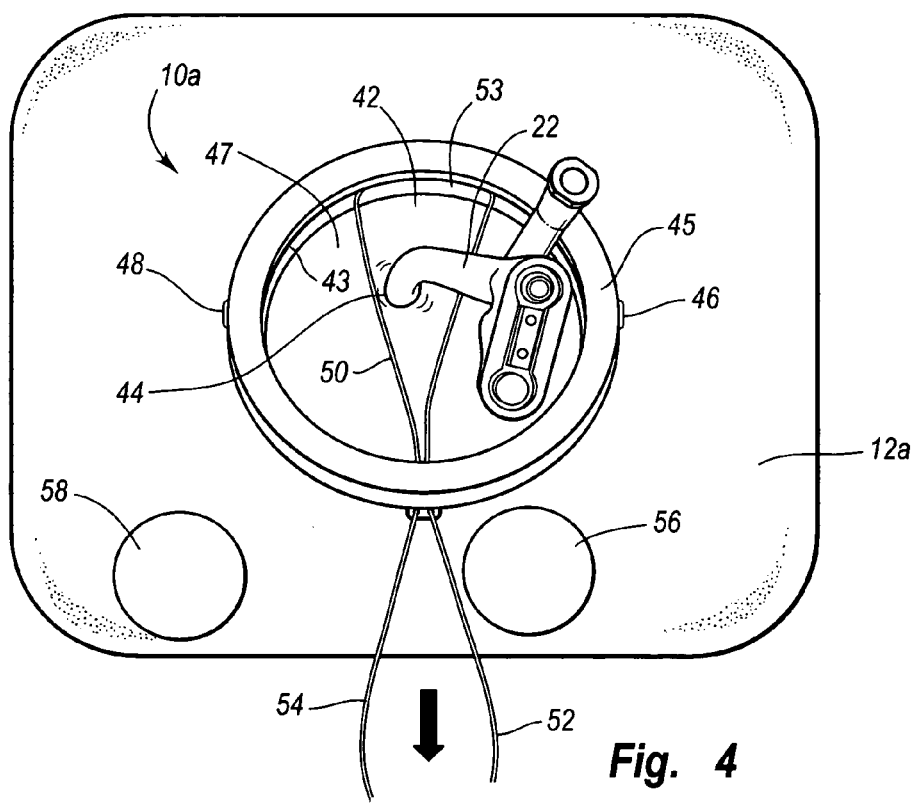
FIG. 4 is a perspective view of the self-suturing anchor device of FIG. 2, illustrating deployment of a first suture.

FIG. 4 illustrates actuation of first suture 50 at the initialization of securing catheter 22. A practitioner first removes adhesive tabs 56 and 58. The practitioner then pulls first end 52 and second end 54 of first suture 50 in a distal direction as indicated. Pulling of the first end 52 and second end 54 in a rearward direction causes a loop portion of first suture 50 to deploy from resilient pocket 43. The loop portion of first suture 50 is configured as a double loop adapted to provide a clove-hitch type of securement arrangement around catheter 22. The illustrated position shows deployment of a single loop of the double loop of first suture 50. The first and second portions of the first loop of first suture 50 are positioned on lateral sides of catheter 22.

Resilient pocket 43 is configured to retain first suture 50 therein until sufficient force is applied to first suture 50 causing first suture 50 to deploy from resilient pocket 43. In one embodiment, resilient pocket 43 includes a retention member and an opening defined by the retention member. In this embodiment, the retention member is positioned circumferentially along the inside diameter of rotatable ring 45 adjacent to resilient pocket 43. The position of the retention member facilitates deployment of sutures 46, 48 and 50 from resilient pocket 43 through the opening defined by the retention member. The retention member is adapted to effectively prevent premature deployment of sutures 46, 48 and 50 from resilient pocket 43 while allowing deployment of sutures 46, 48 and 50 from resilient pocket 43 when sufficient force is exerted on the sutures 46, 48 and 50.

In one embodiment, the retention member includes a top and bottom resilient flange coupled to rotatable ring 45 along the inner circumference of rotatable ring 45 adjacent resilient pocket 43. The two resilient flanges are spaced apart from each other such that the distance between opposing edges of the flanges is less than the diameter of sutures 46, 48 and 50. The positioning of the two resilient flanges prevents sutures 46, 48 and 50 from inadvertently deploying from resilient pocket 43. When sutures 46, 48 and 50 are deployed from resilient pocket 43 through the opening, a portion of at least one of the resilient flanges deflects. Deflection of resilient flanges provides an opening sufficient to allow deploying sutures 46, 48 and 50 to deploy therefrom.

Figure 5:
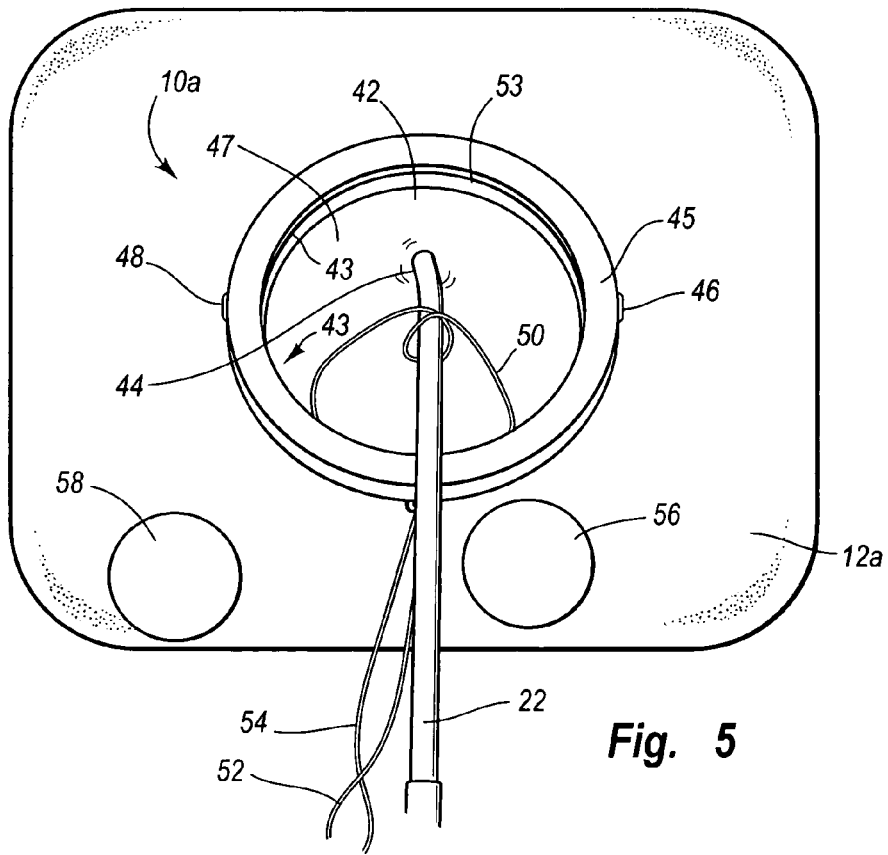
FIG. 5 illustrates the self-suturing anchor device of FIG. 2, as the first suture is tightened into a double loop configuration about the catheter.

FIG. 5 illustrates the configuration of first suture 50 as the second loop of the double loop is being deployed. The second loop deploys as first end 52 and second end 54 are tensioned. Tensioning occurs as first end 52 and second end 54 are retracted further in the distal direction. In the illustrated embodiment, the first loop of first suture 50 has substantially tightened around catheter 22 and the first and second portions of the second loop of first suture 50 are positioned on lateral sides of catheter 22.

Figure 6:
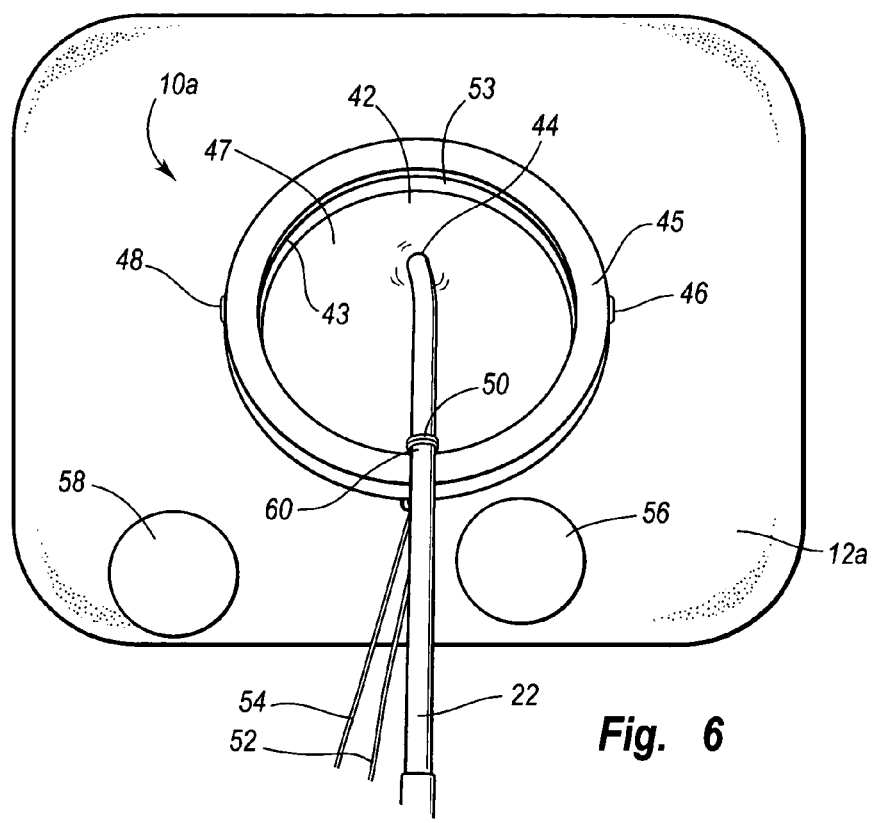
FIG. 6 illustrates the self-suturing anchor device of FIG. 2, after the first suture has been deployed to secure the catheter adjacent a rotatable ring of the anchor device.

FIG. 6 illustrates securement of catheter 22 by first suture 50. In the illustrated embodiment, the double loop clove-hitch configuration of first suture 50 is shown securing catheter 22 to rotatable ring 45 at a bottom securement point 60. By maintaining the tension on first end 52 and second end 54, first suture 50 retains catheter 22 against rotatable ring 45. In this embodiment, first end 52 and second end 54 are tied to catheter 22 at a subsequent step in the securement procedure, as discussed with respect to FIG. 10.

As will be appreciated by those skilled in the art, the time required to secure catheter 22 utilizing first suture 50 (as depicted in FIGS. 3-5) can be as little as a few oz seconds. Not only is time saved in comparison to conventional techniques, but the steps of securing catheter 22 utilizing first suture 50 is conceptually simple, and readily conducted by a surgeon, or by an assisting nurse. As will be appreciated by those skilled in the art, a variety of types and configurations of mechanisms for securing catheter can be utilized without departing from the scope and spirit of the present invention. In one embodiment, the securement of the catheter utilizes a triple loop clove-hitch configuration. In another embodiment, the securement of catheter utilizes two double loop clove-hitch configurations from a first and second suture. In another embodiment, the suture secures the catheter utilizing an arrangement other than a clove-hitch loop. In yet another embodiment, the anchor device includes two or more resilient pockets from which multiple sutures can be deployed to secure the catheter against the rotatable ring.

Figure 7:
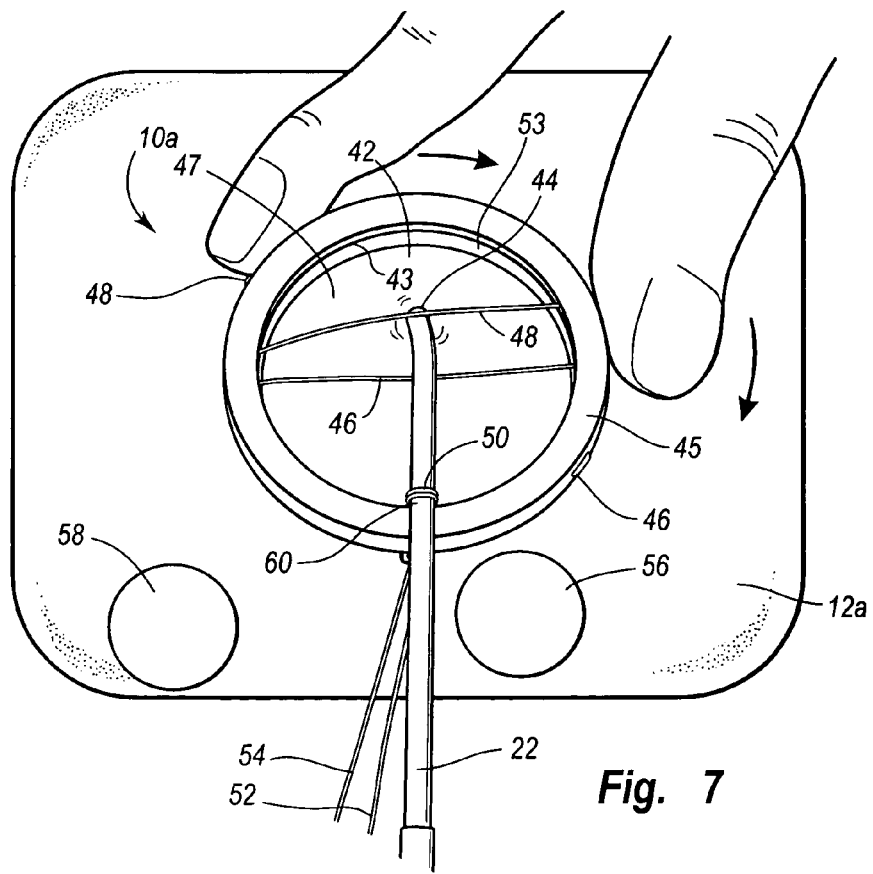
FIG. 7 illustrates an embodiment of the present invention in which the rotatable ring is rotated in order to deploy additional sutures to secure the catheter.

FIG. 7 depicts deployment of second suture 46 and third suture 48 to secure catheter 22 proximate catheter insertion site 44. To actuate sutures 46 and 48, the practitioner rotates rotatable ring 45. In the illustrated embodiment, rotatable ring 45 includes a rotatable outer portion of the ring and a stationary inner portion of the ring which provides the base of the rotatable ring 45. The practitioner rotates rotatable ring 45 in the clockwise direction approximately $\frac{1}{8}^{th}$ of a turn or 45 degrees, as shown by the displacement of the terminal end of second suture 46 relative its position in FIG. 6. This rotation causes a portion of second suture 46 and third suture 48 to deploy from within resilient pocket 43 of rotatable ring 45.

Figure 8:
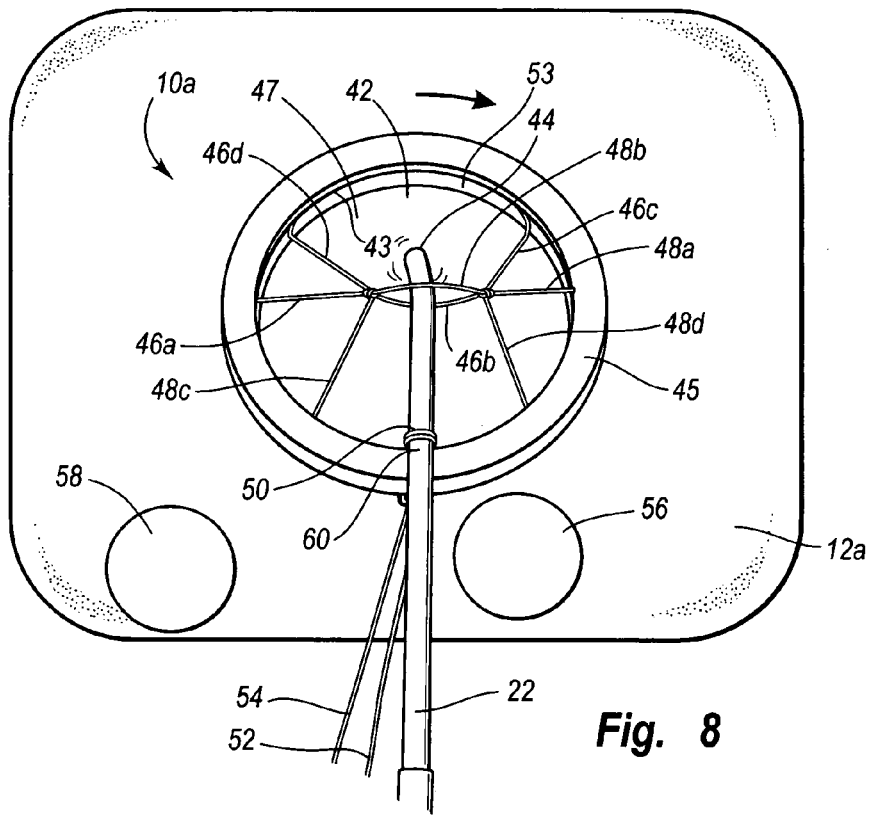
FIG. 8 illustrates the self-suturing anchor device as show in FIG. 7, wherein the rotatable ring is further rotated to draw additional suture loops about the catheter.

FIG. 8 depicts second suture 46 and third suture 48 after additional rotation of rotatable ring 45. The loop formed by second suture 46 is represented by suture portions 46a-d of second suture 46. The loop formed by third suture 48 is represented by suture portions 48a-d of third suture 48. A portion of each of the loops of second suture 46 and third suture 48 has not been completely deployed from resilient pocket 43.

A portion of the loop of each of second suture 46 and third suture 48 are threaded through the slip knot of the opposing suture's loop. In other words, a portion of the loop of second suture 46 is threaded through the slip knot of the loop of third suture 48. Similarly, a portion of the loop of third suture 48 is threaded through the slip knot of the loop of second suture 46. The sharing of opposing slip knots in this manner allows sutures 46 and 48 to cooperatively converge around catheter 22 as they are both pulled. Additionally, the loops pull the opposing knots to converge on the catheter minimizing contact of the loops with the catheter 22 until the loops are completely tightened. This minimizes pressure that would otherwise be exerted on the catheter 22 during closing of the loops. The slip knots of second suture 46 and third suture 48 are one example of a slidable engagement mechanism utilized to form the loops of the sutures.

In the illustrated embodiment, the terminal ends of second suture 46 and third suture 48 are secured to the rotating outer ring 65 of rotatable ring 45. Rotation of rotatable ring 45 moves the terminal ends of second suture 46 and third suture 48 around the circumference of rotatable ring 45. Rotation of rotatable ring 45 pulls the ends of second suture 46 and third suture 48, thus causing the respective perimeters of the loops of both second suture 46 and third suture 48 to be reduced in length. For example, the knot at the terminal end of second suture 46 is moved from the right side of rotatable ring 45 to the left side of rotatable ring 45 during deployment of second suture 46. Similarly, the knot at the terminal end of third suture 48 is moved from the left side of rotatable ring 45 to the right side of rotatable ring 45 during deployment of third suture 48. The rotation of rotatable ring 45 pulls the ends of second suture 46 and third suture 48, further decreasing the size of the loops of second suture 46 and third suture 48. By utilizing rotatable ring 45 to deploy second suture 46 and third suture 48, the loops of second suture 46 and third suture 48 are deployed at the same time and at the same rate preventing unequal securement or unequal forces being exerted on catheter 22 during or subsequent to deployment.

As will be appreciated by those skilled in the art, a variety of types and configurations of mechanisms can be utilized in connection with deployment of the second and third sutures according to the present invention. For example, in one embodiment a slidable engagement mechanism such as a clip, ring, or preformed loop is utilized to form the loops of the first and second sutures. In another embodiment, a single suture is utilized in place of the first and second sutures. In yet another embodiment, three or more sutures are deployed during rotation of the rotatable ring. In yet another embodiment, resilient pocket 43 is formed in rotatable outer ring 65. In yet another embodiment, first and second slot 61 and 63 are positioned in base 72 of rotatable ring 45.

Figure 9:
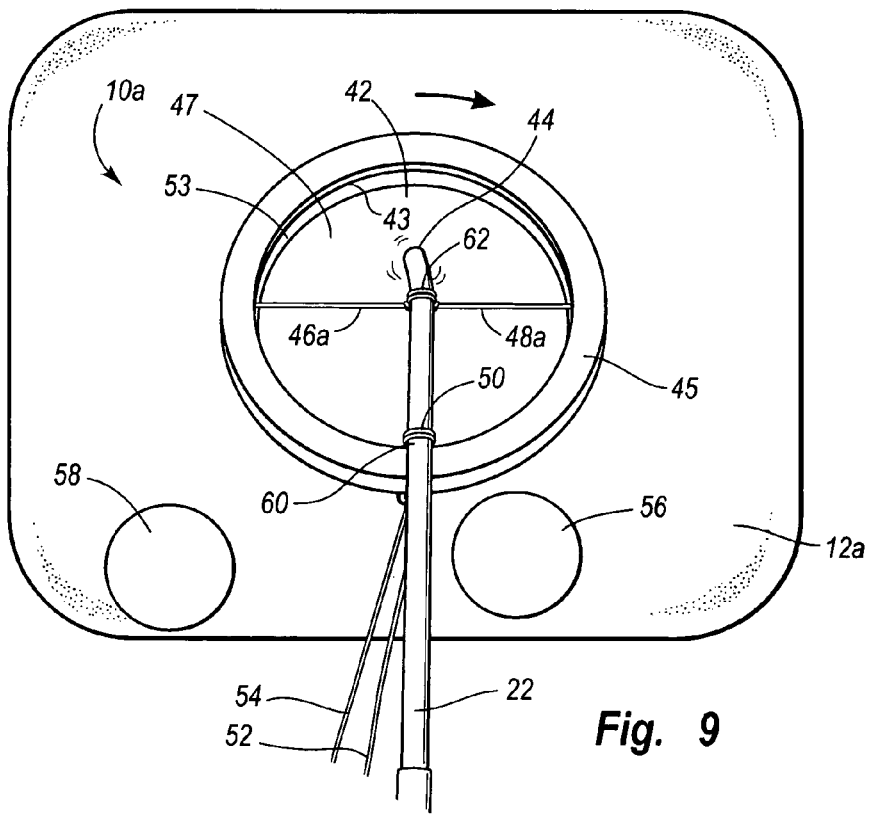
FIG. 9 illustrates the self-suturing anchor device as shown in FIG. 7, wherein the rotatable ring has been rotated such that the additional suture loops have tightened about the catheter.

FIG. 9 illustrates the securement of the portion of catheter 22 positioned adjacent catheter insertion site 44. The slip knot of second suture 46 is securely positioned against the left side of catheter 22. The slip knot of third suture 48 is securely positioned against the right side of catheter 22. The first and second loops formed by second suture 46 and third suture 48 encircle catheter 22 at center securement point 62. The encircling of catheter 22 at center securement point 62 by second suture 46 and third suture 48 minimizes movement of catheter 22 both laterally and in a forward and rearward direction.

As previously discussed, rotating rotatable ring 45 automatically deploys second and third suture 46 and 48 to automatically secure catheter 22 at center securement point 62. As will be appreciated by those skilled in the art, the rotation of rotatable ring 45 is a relatively straightforward task, and can be conducted in a matter of a few seconds.

Once rotatable ring 45 has been rotated sufficient for second and third suture 46 and 48 to secure catheter 22, a practitioner can then tie first and second ends 52 and 54 of first suture 50 to finalize securement of self-suturing anchor device 10a, as illustrated in FIG. 2. Self-suturing anchor device 10a of the present invention allows access to catheter insertion site 44. Access to catheter insertion site 44 allows the practitioner to ascertain the status of the catheter insertion site 44 while also permitting the practitioner, care provider, or patient to properly clean and care for the site.

Self-suturing anchor device 10a also provides a quick and effective mechanism for securing catheter 22 relative to a patient. The practitioner can affix self-suturing anchor device 10a to the patient, actuate suture 50 by pulling first end 52 and second end 54 of first suture 50, actuate sutures 46 and 48 by rotating rotatable ring 45, and then tying ends 52 and 54 of first suture 50 to secure catheter 22 relative to anchor device 10a, all in less than a minute. Additionally, the intuitive nature of actuation of anchor device 10a allows an assisting nurse or other practitioner to secure catheter 22 utilizing anchor device 10a. The present invention provides for automatic securement of catheter 22 in a quick and efficient manner by a practitioner with minimal training and/or requiring minimal effort.

As will be appreciated by those skilled in the art a variety of types and configurations of suture configurations can be utilized without departing from the scope and spirit of the present invention. In one embodiment, more than two suture connections are provided on each side of the catheter between the rotatable ring and the catheter. In another embodiment, one portion of each of the sutures are provided on each of the opposite sides of the catheter in order to provide two suture connections between the rotatable ring and the catheter. In another embodiment, a plurality of suture connections are provided between the catheter and the top and/or bottom sides of the rotatable ring. In yet another embodiment, the anchor device includes multiple resilient pockets configured to receive, house and allow selective deployment of a plurality of sutures. In this embodiment, multiple sutures are deployed from within at least one resilient pocket to secure the catheter against the rotatable ring. In another embodiment a rotatable ring having a plurality of rotatable components allows independent rotation of the plurality of components to deploy different sutures from different pockets.

Figure 10:
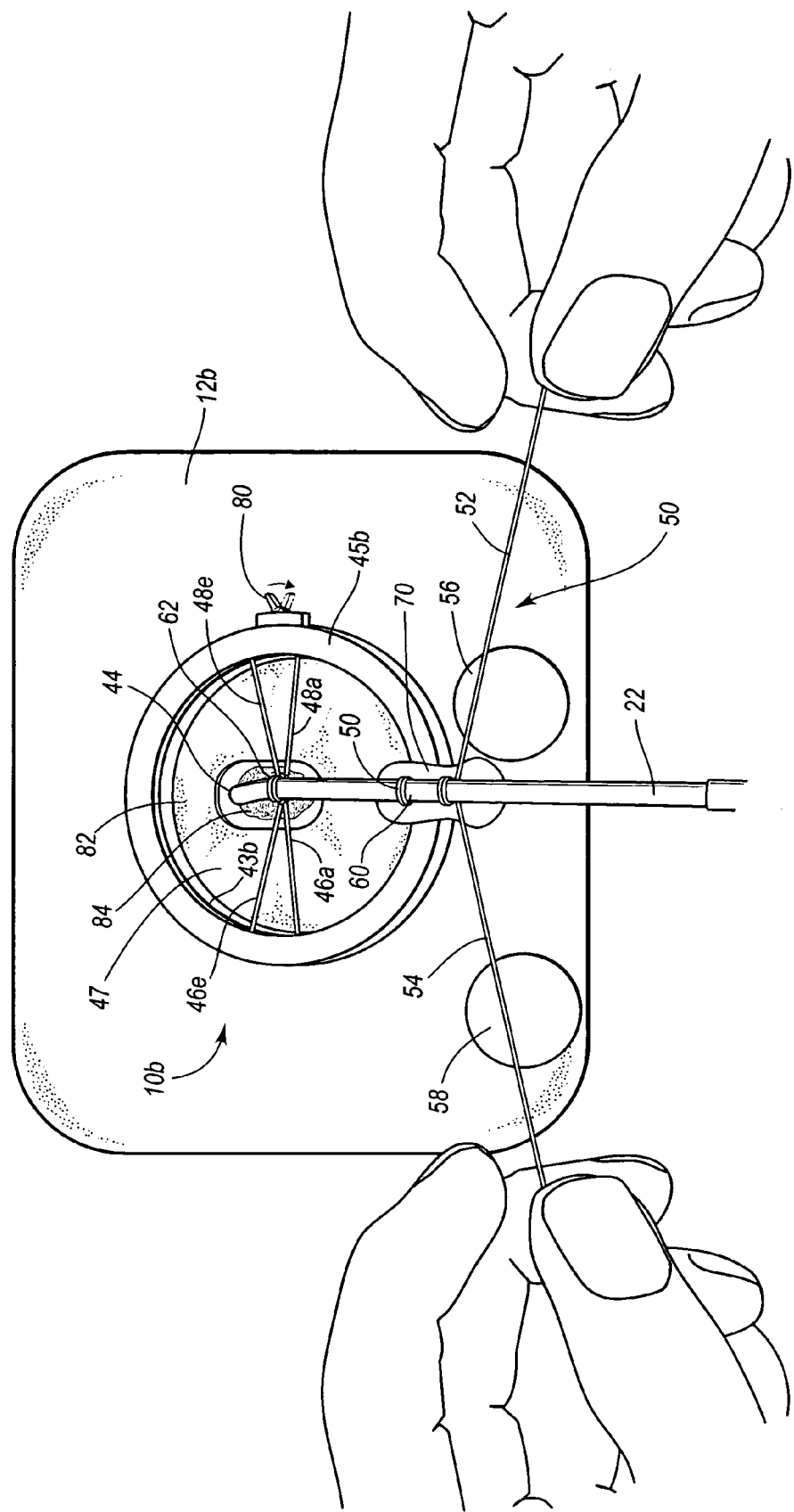
FIG. 10 illustrates an embodiment of a self-suturing anchor device having an anti-microbial patch and a saddle.

FIG. 10 illustrates a self-suturing anchor device 10b according to an alternative embodiment of the present invention. In the illustrated embodiment, self-suturing anchor device 10b is depicted subsequent to deployment of first, second and third sutures 50, 46 and 48. Second suture 46 and third suture 48 secure catheter 22 at center securement point 62. In the illustrated embodiment, second suture 46 secures center securement point 62 relative to rotatable ring 45b utilizing second suture portions 46a and 46e. Third suture 48 secures center securement point 62 relative to rotatable ring 45b utilizing third suture portions 48a and 46e. Undesired movement of catheter is minimized by utilizing two suture portions on each side of catheter 22 to secure catheter 22 relative to rotatable ring 45b.

In the illustrated embodiment, suture portions 46a and 46e comprise two portions of the same suture thread, and are associated with a single loop portion of suture 46. Similarly, in the illustrated embodiment suture portions 48a and 48e comprise two portions of the same suture thread, and are associated with a single loop portion of suture 48. In an alternative embodiment of the present invention, suture portions 46a and 46e comprise separate suture threads, and are associated with separate loop portions, and suture portions 48a and 48e comprise separate suture threads, and are associated with separate loop portions. In the illustrated embodiment, sutures 46 and 48 are formed using 4.0 silk suture material. As will be appreciated by those skilled in the art, a variety of types and configurations of suture material can be utilized with the self-suturing anchor device.

Self-suturing anchor device 10b includes a locking lever 80, an adhesive layer 82, and an anti-microbial patch 84. Locking lever 80 is adapted to lock the rotational position of rotatable ring 45b. This allows the user to selectively lock rotatable ring 45b to maintain a desired amount of tension on sutures 46 and 48 to secure catheter 22. As will be appreciated by those skilled in the art, a variety of types and configurations of locking mechanisms can be utilized without departing from the scope and spirit of the present invention. In one embodiment, a locking button is provided that can be depressed to lock the position of rotatable ring 45b relative to other components of self-suturing anchor 10b.

Adhesive layer 82 is provided to contact the patient's skin at center aperture 47. In the illustrated embodiment, adhesive layer 82 includes a small aperture allowing a practitioner to observe catheter insertion site 44. In one embodiment, the adhesive layer 82 is transparent or semi-transparent to allow a practitioner to observe the catheter insertion site 44. Adhesive layer 82 can provide additional securement of catheter 22 relative to the patient. Additionally, anti-microbial or other properties can be imbued in adhesive layer 82 to minimize infection of insertion site 44.

Anti-microbial patch 84 is positioned adjacent catheter insertion site 44. Anti-microbial patch 84 minimizes infection at catheter insertion site 44. Anti-microbial patch 84 can also be configured to absorb blood or fluids that leak from catheter insertion site 44. Anti-microbial patch 84 can be utilized either alone or in combination with adhesive layer 82. As will be appreciated by those skilled in the art, a variety of types and configurations of adhesive covers and anti-microbial patches can be utilized without departing from the scope and spirit of the present invention.

A foam cushion 70 is shown at the point of contact between rotatable ring 45b and catheter 22. Foam cushion 70 is utilized to buffer contact between rotatable ring 45b and catheter 22. Foam cushion 70 provides a gradual flow over the upper surface of rotatable ring 45b. Furthermore, foam cushion 70 minimizes kinking, pinching, and/or other obstruction that results in the decrease of fluid flow through the drainage catheter that is caused by the contact between catheter 22 and rotatable ring 45b. Additionally, where a patient lays or rests against a surface that contacts catheter 22 at or adjacent the point of contact with rotatable ring 45b, foam cushion 70 can diffuse the pressure exerted on the patient by the combination of catheter 22 and rotatable ring 45b.

As will be appreciated by those skilled in the art, a variety of types and configurations of cushioning mechanism can be utilized with the rotatable ring without departing from the scope and spirit of the present invention. In one embodiment, a resilient rubber or gel layer is provided between the catheter and the rotatable ring. In another embodiment, the rotatable ring is flexible, resilient, or otherwise deformable to provide a layer of cushion between the patient and catheter. In another embodiment, a cushion layer is additionally provided between the rotatable ring and the patient.

Figure 11A:
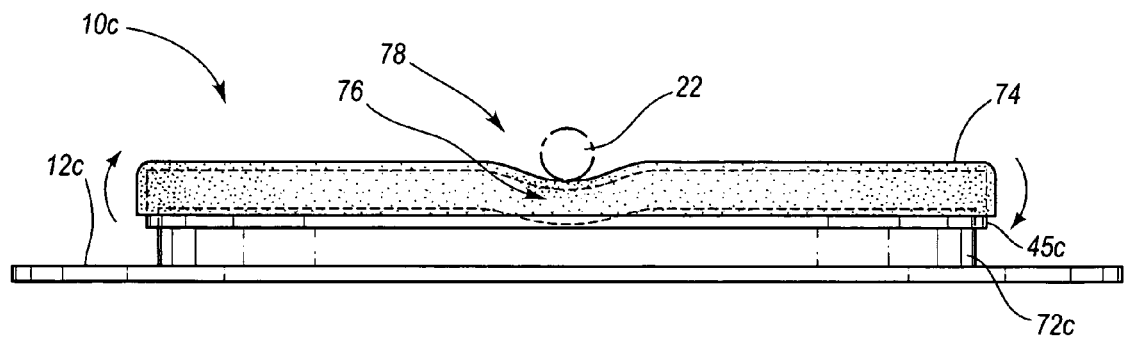
FIG. 11A illustrates an embodiment of a self-suturing anchor device having a cushion layer and depicting the rotatable ring in an unlocked position.
Figure 11B:
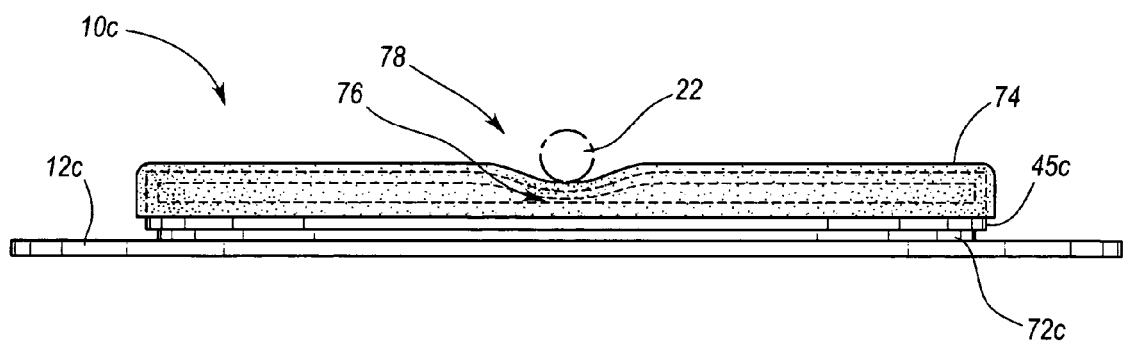
FIG. 11B illustrates the self-suturing anchor device of FIG. 11A wherein rotatable ring is in a locked position.

FIGS. 11A and 11B are side views of a self-suturing anchor device 10c according to another embodiment of the present invention. In the illustrated embodiment, rotatable ring 45c is adapted to be selectively locked to prevent rotation of rotatable ring 45c. In the illustrated embodiment, rotatable ring 45c is utilized with a stationary inner ring, or base 72c. Base 72c is secured to adhesive sheet 12c. Rotatable ring 45c can be rotated relative to base 72c. To lock rotatable ring 45c the user exerts a downward force on rotatable ring 45c such that rotatable ring 45c is pushed in a downward direction and substantially covers base 72c. When rotatable ring 45c covers base 72c as depicted in FIG. 11B, rotation of rotatable ring 45c is prevented. Preventing rotation of rotatable ring 45c subsequent to securement of catheter 22 minimizes loosening of the sutures utilized to secure catheter 22. Locking rotatable ring 45c in this manner allows the user to maintain the degree and amount of securement of catheter 22 subsequent to actuation of self-suturing anchor device 10c.

As will be appreciated by those skilled in the art, a variety of types and configurations of mechanisms for preventing rotation of the rotatable ring can also be utilized without departing from the scope and spirit of the present invention. For example, in one embodiment, rotation of the rotatable ring is prevented by friction between the rotatable ring and the base. In another embodiment, rotation of the rotatable ring is prevented by interlocking engagement between the rotatable ring and the base. In yet another embodiment, the rotatable ring is configured to rotate in a ratcheting fashion, such that the rotatable ring is adapted to rotate in one direction and prevented from rotating in the other direction. In yet another embodiment, the rotatable ring is unlocked when the rotatable ring substantially covers base, and is locked when the rotatable ring is in a raised position with respect to base.

Rotatable ring 45c includes a cushion layer 74. Cushion layer 74 substantially covers and overlays rotatable ring 45c. Cushion layer 74 provides padding to minimize discomfort when a patient lays or rests on a surface in contact with self-suturing anchor device 10c. Additionally, cushion layer 74 can help to minimize kinking or pinching of catheter 22 by contact with rotatable ring 45c, or other obstruction causing a reduction of fluid flow through catheter 22. A variety of types and configurations of cushion layers can be utilized without departing from the scope and spirit of the present invention, including but not limited to resilient foam, gel, thermoplastics, rubber, latex, and the like.

In the illustrated embodiment, a saddle 76 is formed in rotatable ring 45c and a saddle 78 is formed in cushion layer 74 to accommodate catheter 22. The shape of saddles 76 and 78 minimize the exposure of catheter 22 above the upper surface of cushion layer 74 and rotatable ring 45c. Cushion layer 74 can also be deformed such that catheter 22 is minimally exposed above the upper surface of cushion layer 74. As a result, saddles 76 and 78 help minimize kinking or pinching of catheter 22, or the restriction of fluid flow through catheter 22 while decreasing discomfort that may be created by laying or contacting portions of self-suturing anchor device 10c.

Figure 12A:
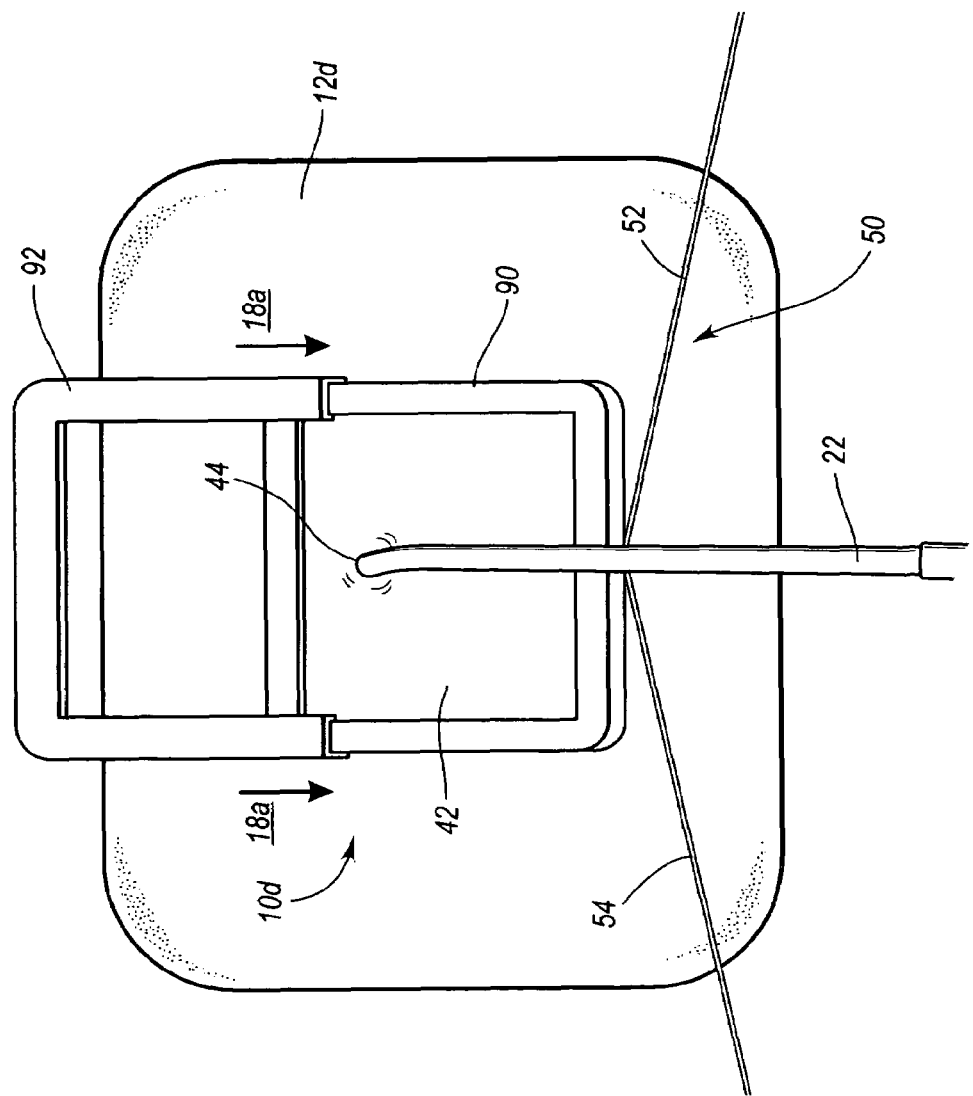
FIG. 12A illustrates an embodiment of a self-suturing anchor having a square configuration; and, FIG. 12B illustrates the self-suturing anchor device as shown in FIG. 12A, in which the sutures have been deployed to secure catheter relative to the anchor device.

FIGS. 12A and 12B illustrate a self-suturing anchor device 10d according to still another embodiment of the present invention. In the illustrated embodiment, self-suturing anchor device 10d utilizes a suture deployment base 90, and a slidable portion 92. Suture deployment base 90 has a square configuration and provides a similarly-shaped aperture circumscribing catheter insertion site 44. Slidable portion 92 slidably engages the upper portion of suture deployment base 90. First suture 50 is positioned adjacent the bottom end of suture deployment base 90. First suture 50 is deployable in similar manner to that depicted and described with respect to rotatable ring 45 of FIGS. 4, 5 and 6.

To deploy second suture 46 and third suture 48, a user moves slidable portion 92 in the direction of directional arrows 18a. As the user moves slidable portion 92 in the direction of directional arrows 18a, sutures 46 and 48 are deployed in a manner similar to that depicted and described with respect to FIGS. 7, 8 and 9. The ends of suture 46 and 48 pass through the upper portion of suture deployment base 90. As a result, movement of slidable portion 92 in the direction of directional arrows 18a pulls sutures 46 and 48 along the length of the sides of suture deployment base 90. This reduces the size of the loops formed in sutures 46 and 48.

Once slidable portion 92 is moved, such that slidable portion 92 is substantially aligned with suture deployment base 90, catheter 22 is secured by sutures 46 and 48 as depicted in FIG. 12B. In the illustrated embodiment a four inch by four inch (4"×4") adhesive patch (not shown) can be positioned over self-suturing anchor device 10d, to facilitate additional securement of catheter 22 relative to the patient. In one embodiment, a portion of the adhesive patch is transparent, allowing a user to view the condition of the catheter insertion site 44.

As will be appreciated by those skilled in the art, a variety of types and configurations of self-suturing anchor devices can be provided, without departing from the scope and spirit of the present invention. For example, in one embodiment, the suture deployment device is a rectangular configuration. In another embodiment, the base of the suture deployment device has a different shape than the rotatable or slidable member. In another embodiment, the adhesive sheet is circular, rectangular, or of a different size or configuration. In still another embodiment, the size of the adhesive sheet utilized to overlay the suture deployment device varies. In yet still another embodiment, the type and configuration of sutures utilized to secure the catheter are adapted to the type of catheter to be secured, and can be varied. In another embodiment, the self-suturing anchor device comprises both a slidable portion and a rotatable portion used in conjunction to comprise the suture deployment device.

In general, securement means are directed primarily to sutures, strings, cords, wires, bands, adhesive strips, rigid elements, or other securement mechanisms that are configured to tighten one or more sutures about a first securement point of a catheter by a user actuating at least a portion of the securement means. The securement means can also include specific device elements configured to tension one or more sutures to secure a second securement point of the catheter against a portion of the catheter anchor device.

For example, to accomplish the function of securement, the relevant device means can include a rotatable ring (e.g., 45) where one of the sutures (e.g., 46 or 48) is secured to a portion of the rotatable ring on one end, and also secured to itself (e.g., with a slip knot joining suture portions 46a, 46d, and 48c, or suture portions 46c, 48a, and 48d) on an opposing end inside a resilient pocket (e.g., 43). Accordingly, the securement means provide that, as the one end (e.g., 46, 48) is moved, the corresponding suture (e.g., 46a-e, 48a-e) is configured to come out of the one or more resilient pockets (e.g., 43), and slidably tighten about a catheter 22 positioned inside the central aperture.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A catheter anchor device for use with a catheter which is inserted into a patient at a catheter insertion site for minimizing movement of the catheter that could result in pressure, discomfort, or tearing at the catheter insertion site, the catheter anchor device configured to automatically deploy one or more sutures to quickly and efficiently secure the catheter, the anchor device comprising:

an adhesive layer configured to be secured to the skin of the patient proximate the catheter insertion site and having a center aperture surrounding the catheter insertion site that allows access to the catheter insertion site and permits a practitioner to view and clean the catheter insertion site without manipulating or removing the adhesive layer;

at least one semi-rigid securement mechanism coupled to the adhesive layer and having one or more recesses formed therein, the at least one semi-rigid securement mechanism providing access to the center aperture;

one or more sutures positioned within the one or more recesses, the one or more sutures being secured to the at least one semi-rigid securement mechanism; and a movable member being utilized in connection with the one or more sutures, wherein movement of the movable member automatically deploys the one or more sutures from the one or more recesses and secures the catheter relative to the anchor device.

2. The anchor device as recited in claim 1, wherein the movable member comprises a portion of the at least one semi-rigid securement mechanism.

3. The anchor device as recited in claim 2, wherein the semi-rigid securement mechanism and the movable member comprise a rotatable ring.

4. The anchor device as recited in claim 1, further comprising an anti-microbial patch positioned adjacent the catheter insertion site.

5. The anchor device as recited in claim 1, wherein the one or more sutures comprise first and second looped sutures configured to secure a first securement point of the catheter.

6. The anchor device as recited in claim 5, wherein the first looped suture is threaded through a second slidable securement mechanism of the second looped suture, and wherein the second looped suture is threaded through a first slidable securement mechanism of the first looped suture.

7. The anchor device as recited in claim 5, wherein the one or more sutures further comprise at least a third looped suture configured to slidably secure a second securement point of the catheter.

8. The anchor device as recited in claim 7, wherein the third looped suture is adapted to be secured to the semi-rigid securement mechanism.

9. The anchor device as recited in claim 1, wherein the at least one semi-rigid securement mechanism and the movable member comprise a rotatable ring and wherein the semi-rigid securement mechanism comprises a fixed inner ring, and wherein the movable member comprises a rotatable outer ring.

10. The anchor device as recited in claim 9, wherein one end of the one or more sutures is secured to the rotatable ring, such that rotation of the outer ring with respect to the inner ring causes the one or more sutures to deploy from the one or more recesses.

11. The anchor device as recited in claim 9, wherein the rotatable ring includes a flexibly resilient saddle adapted to be in contact with the catheter.

12. The anchor device as recited in claim 9, wherein further comprising a locking mechanism adapted to secure the rotational position rotatable ring.

13. The anchor device as recited in claim 1, wherein the semi-rigid securement mechanism comprises a suture deployment base, and wherein the movable member comprises a slidable portion configured to linearly slide with respect to the suture deployment base.

14. The anchor device as recited in claim 13, wherein one end of the one or more sutures is secured to the slidable portion, such that movement of the slidable portion with respect to the suture deployment base causes the one or more sutures to come out of the one or more recesses, and slidably tighten about a catheter positioned inside the center aperture.

15. In a medical environment in which a medical catheter is employed, a catheter anchor device configured to secure a catheter to the anchor device with one or more sutures, comprising:
 a base having a securement mechanism, the securement mechanism having one or more resilient pockets formed therein; and
 a plurality of sutures positioned within the one or more resilient pockets; and
 securement means configured to tighten the at least one of the plurality of sutures about a first securement point of a catheter positioned within the securement mechanism by moving at least a portion of the securement mechanism, the securement means further configured such that tensioning of at least a second of the plurality of sutures secures a second securement point of the catheter against the securement mechanism.

16. The catheter anchor device as recited in claim 15, wherein the securement means comprises:
 at least one of the plurality of sutures being secured against the securement mechanism on one end and secured to itself on an opposing end inside a resilient pocket;
 wherein, as the one end is moved, the corresponding one of the plurality of sutures is configured to deploy from the one or more resilient pockets, and slidably tighten about a catheter positioned inside a central aperture of the anchor device.

17. In a medical environment in which a medical catheter is employed, a catheter anchor device configured to secure a catheter to the anchor device with one or more sutures, wherein the sutures are applied in a minimal time frame, comprising:
 an adhesive pad;
 a rotatable ring rotatably linked to the adhesive pad;
 a circular recess formed within the rotatable ring, the recess configured: (i) to receive and house a suture therein; and (ii) to allow selective deployment of a suture therefrom; and
 a plurality of sutures positioned within the recess, such that rotation of the rotatable ring deploys at least one of the plurality of sutures from the recess to secure the catheter relative to the anchor device.

18. The catheter anchor device as recited in claim 17, further comprising a foam cushion positioned between the catheter and rotatable ring to act as a buffer.

19. The catheter anchor device as recited in claim 17, wherein the rotatable ring comprises a cushion layer to act as a buffer between the rotatable ring and the catheter.

20. A catheter anchor device configured to automatically deploy one or more sutures to secure a catheter, the anchor device comprising:
 an adhesive layer configured to be secured to a patient;
 a securement mechanism having a base portion and a movable portion; and
 at least one suture utilized in connection with the securement mechanism wherein movement of the movable portion relative to the base portion automatically deploys the at least one suture and secures the catheter relative to the anchor device.

* * * * *